US009539367B2

(12) United States Patent
Britigan et al.

(10) Patent No.: US 9,539,367 B2
(45) Date of Patent: Jan. 10, 2017

(54) GALLIUM INHIBITS BIOFILM FORMATION

(75) Inventors: Bradley E. Britigan, Cincinnati, OH (US); Pradeep K. Singh, Iowa City, IA (US)

(73) Assignee: University of Iowa Research Foundation, Iowa City, IA (US)

(*) Notice: Subject to any disclaimer, the term of this patent is extended or adjusted under 35 U.S.C. 154(b) by 3423 days.

(21) Appl. No.: 11/004,049

(22) Filed: Dec. 3, 2004

(65) Prior Publication Data

US 2006/0018945 A1    Jan. 26, 2006

Related U.S. Application Data

(60) Provisional application No. 60/526,907, filed on Dec. 4, 2003.

(51) Int. Cl.

| | | |
|---|---|---|
| *A61L 27/54* | (2006.01) | |
| *A61K 31/28* | (2006.01) | |
| *A61K 33/24* | (2006.01) | |
| *A01N 59/16* | (2006.01) | |
| *A61L 27/30* | (2006.01) | |
| *A61L 29/10* | (2006.01) | |
| *A61L 29/16* | (2006.01) | |

(52) U.S. Cl.
CPC ............... *A61L 27/54* (2013.01); *A01N 59/16* (2013.01); *A61K 31/28* (2013.01); *A61K 33/24* (2013.01); *A61L 27/306* (2013.01); *A61L 29/106* (2013.01); *A61L 29/16* (2013.01); *A61L 2300/102* (2013.01); *A61L 2300/404* (2013.01)

(58) Field of Classification Search
CPC ............................... A61K 31/28; A61K 33/24
USPC ........................................... 514/492; 424/650
See application file for complete search history.

(56) References Cited

U.S. PATENT DOCUMENTS

| | | | | |
|---|---|---|---|---|
| 5,688,516 | A | 11/1997 | Raad et al. | 424/409 |
| 5,997,912 | A | 12/1999 | Schlesinger et al. | 424/650 |
| 6,086,921 | A | 7/2000 | Domenico | 424/653 |
| 6,190,407 | B1 | 2/2001 | Ogle et al. | 623/1.51 |
| 6,203,822 | B1 | 3/2001 | Schlesinger et al. | 424/650 |
| 6,267,782 | B1 | 7/2001 | Ogle et al. | 623/1.1 |
| 6,267,979 | B1 | 7/2001 | Raad et al. | 424/405 |
| 6,716,895 | B1* | 4/2004 | Terry | 523/122 |
| 2002/0068761 | A1 | 6/2002 | Bernstein | 514/460 |
| 2005/0158263 | A1* | 7/2005 | Rioux et al. | 424/70.1 |

FOREIGN PATENT DOCUMENTS

| | | |
|---|---|---|
| JP | H05-503924 | 6/1993 |
| JP | H08-337506 | 12/1996 |
| JP | 2001-200469 | 7/2001 |
| JP | 2002-356652 | 12/2002 |
| WO | WO92/18098 | * 10/1992 |
| WO | WO 98/09622 | 3/1998 |
| WO | WO 00/47214 | 8/2000 |
| WO | WO 01-43788 | 6/2001 |
| WO | WO 03/053347 | 7/2003 |
| WO | WO 03/088914 | 10/2003 |
| WO | WO 2004/028406 | 4/2004 |

OTHER PUBLICATIONS

Nield-Gehrig, J.S. Dental Plaque Biofilms presentation, 2003.*
U.S. Appl. No. 10/958,923, filed Oct. 4, 204, Singh, et al.
Bernstein, "Mechanisms of Therapeutic Activity for Gallium," *Pharmacol. Rev.*, 50:665-682, 1998.
Chitambar, "Gallium Nitrate Revisited," *Semin Oncol.*, 30:1-4, 2003.
Chitambar et al., "Inhibition of Leukemic HL60 Cell Growth by Transferrin-Gallium: Effects on Ribonucleotide Reductase and Demonstration of Drug Synergy with Hydroxyurea," *Blood*, 72:1930-1936, 1988.
Chitambar et al., "Uptake of Gallium-67 by Human Leukemic Cells: Demonstration of Transferrin Receptor-dependent and Transferrin-independent Mechanisms," *Cancer Res.*, 47:3929-3934, 1987.
Foster et al., "Gallium Nitrate: The Second Metal With Clinical Activity," *Cancer Treat Rep.*, 70:1311-1319, 1986.
Hubbard et al., "Effects of iron-limitation of *Escherichia coli* on growth, the respiratory chains and gallium uptake," *Arch. Microbiol.*, 146:80-86, 1986.
Jonkoff et al., "Gallium-67 radiotoxicity in human U937 lymphoma cells," *Br. J. Cancer*, 67:693-700, 1993.
Leyland-Jones, "Pharmacokinetics and Therapeutic Index of Gallium Nitrate," *Semin Oncol.*, 18:16-20, 1991.
Narasimhan et al., "Effect of Gallium on the Tyrosyl Radical of the Iron-Dependent M2 Subunit of Ribonucleotide Reductase," *Biochem. Pharmacol.*, 44:2403-2408, 1992.
Olakanmi et al., "Gallium Disrupts Iron Metabolism of Mycobacteria Residing within Human Macrophages," *Infect. Immun.*, 68:5619-5627, 2000.
Olakanmi et al., "Acquisition of Iron Bound to Low Molecular Weight Chelates by Human Monocyte-Derived Macrophages," *J. Immunol.* 153:2691-2703, 1994.
Schmitt et al., "Characterization of an Iron-Dependent Regulatory Protein (IdeR) of *Mycobacterium tuberculosis* as a Functional Homolog of the Diphtheria Toxin Repressor (DtxR) from *Corynebacterium diphtheriae*," *Infect. Immun.*, 63:4284-4289, 1995.
Seligman et al., "Treatment with Gallium Nitrate: Evidence for Interference With Iron Metabolism In Vivo," *Am. J. Hematol.*, 41:232-240, 1992.
Singh et al., "A component of innate immunity prevents bacterial biofilm development," *Nature*, 417:552-555, 2002.
Todd et al., "Gallium Nitrate," *Drugs*, 42:261-273, 1991.

(Continued)

*Primary Examiner* — Jeffrey S Lundgren
*Assistant Examiner* — Sara E Townsley
(74) *Attorney, Agent, or Firm* — Norton Rose Fulbright US LLP

(57) ABSTRACT

The present invention provides a gallium-containing composition for coating/impregnating a device or device surface to prevent biofilm growth formation. The present invention also provides a method of preventing or inhibiting biofilm growth formation. The present invention also provides methods for killing established biofilms.

13 Claims, 11 Drawing Sheets

(56) References Cited

OTHER PUBLICATIONS

Yang et al.,"Isolation of Ribonucleotide Reductase from *Mycobacterium tuberculosis* and Cloning, Expression, and Purification of the Large Subunit," *J. Bacteriol.*, 176:6738-6743, 1994.
Yang et al., "Characterization of Two Genes Encoding the *Mycobacterium tuberculosis* Ribonucleotide Reductase Small Subunit," *J. Bacteriol.*, 179:6408-6415, 1997.
Eby, "Is navicular disease in horses curable using gallium nitrate? Yes, if treatment is started sufficiently early—with lameness controlled in serious cases," located at http://george-eby-research.com/html/nav.html, downloaded Sep. 10, 2008.
Eby, "Is navicular disease in horses curable with gallium nitrate? We will see!" located at http://web.archive.org/web/19970105114212/http://www.coldcure.com/html/nav.html, Jan. 5, 1997 entry located by searching "http://coldcure.com/html/nav.html" on archive website http://archive.org, downloaded Sep. 10, 2008.
Email letter from George Eby, Subject: Undisclosed prior art for WO/2007/053581—Growth control of oral and superficial microorganisms using gallium compounds, mailed to Charles E. Miller on Sep. 9, 2008.
Anwar et al., "Establishment of aging biofilms: Possible mechanism of bacterial resistance to antimicrobial therapy," *Antimicrobial Agents and Chemotherapy*, 36(7):1347-1351, 1992.
Costerton et al., "Bacterial biofilms: A common cause of persistent infections," *Science*, 284:1318-1322, 1999.
Moorthy et al., "Identification of novel stage-specific genetic requirements through whole genome transcription profiling of *Vibrio cholerae* bioflim development," *Molecular Microbiology*, 57(6):1623-1635, 2005.
Olson et al., "Biofilm bacteria: formation and comparative susceptibility to antibiotics," *The Canadian Journal of Veterinary Research*, 66:86-92, 2002.
Office Communication, issued in New Zealand Patent Application No. 547884, dated May 28, 2009.
Office Communication, issued in Australian Patent Application No. 2004296178, dated Sep. 15, 2009.
Office Communication, issued in Australian Patent Application No. 2004296178, dated Jul. 14, 2010.
Chitambar, "Medical applications and toxicities of gallium compounds" *International Journal of Environmental Research and Public Health*, 7:2337-2361, 2010.
Francesca et al., "Both lactoferrin and iron influence aggregation and biofilm formation in *Streptococcus mutans*," *BioMetals*, 17:271-278, 2004.
Ubertalli, James T. DMD, "Gingivitis," *The Merk Manuals Online Medical Library*, available online at http://www.merck.com/mmhe/print/sec08/ch115/ch115b.htmlrl, Oct. 2008.
Hoffman et al., "Aminoglycoside antibiotics induce bacterial biofilm formation," *Nature Letters*, 436:1171-1175, 2005.
Johnson et al., "Iron-regulated biofilm formation in *Staphylococcus aureus* Newman requires *ica* and the secreted protein EMP," *Infection and Immunity*, 76(4):1756-1765, 2008.
Johnson et al., "Iron-responsive regulation of biofilm formation in *Staphylococcus aureus* involves fur-dependent and fur-independent mechanisms," *Journal of Bacteriology*, 187(23):8211-8215, 2005.
Linares et al., "Antibiotics as intermicrobial signaling agents instead of weapons" *PNAS*, 103(51):19484-49489, 2006.
Prince, "Biofilms, Antimicrobial resistance, and airway infection," *N. Eng. J. Med.*, 347(14):1110-111, 2002.
Stewart, "Mechanisms of antibiotic resistance in bacterial biofilms," *Int. J. Med. Micorbiol.*, 292:107-113, 2002.
Office Communication, issued in Indian Patent Application No. 3724/DELNP/2006, dated Feb. 3, 2011.
Office Communication, issued in Japanese Patent Application No. 2006-542790, dated Apr. 25, 2011. (English translation).
Office Communication issued in Canadian Patent Application No. 2,547,982, dated Jul. 4, 2011.
Office Communication issued in Chinese Patent Application No. 200480039693, dated Jun. 22, 2011. (English translation).
Office Communication issued in Japanese Patent Application No. 2006-542790, dated Jun. 11, 2012. (English translation).

\* cited by examiner

GALLIUM INHIBITS BIOFILM FORMATION

This application claims the benefit of priority to U.S. Provisional Patent Application No. 60/526,907 filed on Dec. 4, 2003, which is hereby incorporated by reference in its entirety.

The government may own rights in the present invention pursuant to grant number RO1 A134954 and KO8HL-041173 from the National Institutes of Health.

BACKGROUND OF THE INVENTION

1. Field of the Invention

The present invention relates generally to the medical and industrial fields. More particularly, it concerns a gallium-containing composition to prevent or inhibit biofilm growth formation and infections arising therefrom.

2. Description of Related Art

Bacterial contamination of medical devices are commonly caused by biofilm formation which leads to infections such as nosocomial infections. Nosocomial pneumonia is the second most common nosocomial infection, and is associated with the highest attributable mortality and morbidity. For example, the risk of nosocomial pneumonia has dramatically increased over the years from the use of mechanical ventilation equipment (Official Statement, American Thoracic Society). Nosocomial infections, especially those involving the bloodstream or lung often cause death.

Population-based surveillance studies of nosocomial infections in U.S. hospitals indicate a 5% attack rate or incidence of 5 infections per 1,000 patient-days (Wenzel et al., 2001). The Surveillance and Control of Pathogens of Epidemiologic Importance (SCOPE) surveillance system of nosocomial bloodstream infections in U.S. hospitals identified a crude mortality rate of 27%, with great variation by pathogen. Estimates of nosocomial bloodstream infections from the SCOPE database indicate that 70% occur in patients with central venous catheters (Wenzel et al., 1999). SCOPE has identified that 49% of all nosocomial bloodstream infections occur in intensive-care units where patients often have weakened immune systems and are frequently on ventilators and/or catheters on which bacteria often form biofilms.

Nosocomial pneumonia is also commonly caused by endotracheal tubes which are common vehicles for bacterial colonization/contamination leading to biofilm growth formation. The endotracheal tube connects the oropharyngeal environment with the sterile bronchoalveolar space, significantly increasing the risk of nosocomial pneumonia. Formation of biofilms within endotracheal tubes plays a role in the initiation of ventilator-associated pneumonia and may select for antibiotic resistance among bacterial species causing such infections (Sottile et al., 1986; Inglis et al., 1989; Adair et al., 1993; Koerner et al., 1998; Gorman et al., 2001; Adair et al., 1999).

A primary contributor to nosocomial bloodstream infections are vascular catheters. It is estimated that around 400,000 vascular catheter-related bloodstream infections (CRBSI) occur annually in the United States (Raad, 1998). Another frequent causes of nosocomial infections are urinary tract infections (UTI), which contribute to 34% of all nosocomial infections (Klempner et al., 1998). Nosocomial UTI are usually associated with contamination of urinary catheters.

In addition, nosocomial infections due to biofilm growth formation are common complications of surgical procedures, particularly in cancer and immunocompromised patients with devitalized tissue and decreased immunity. Surgical wound infections contribute to 17% of all nosocomial infections (Platt and Bucknall, 1988). Many surgical wound infections are associated with the bacterial contamination of sutures.

Antibiotics and antiseptics have been used to coat/impregnate devices on which bacteria may grow and form biofilms, leading to infection such as nosocomial infections. However, although these infections can be controlled for many years by antibiotics, ultimately the bacteria (e.g., *P. aeruginosa*) form a biofilm that is resistant to antibiotic treatment therefore rendering these agents therapeutically ineffective. The durability of existing antiseptics in controlling biofilm formation has also been limited.

Several studies have examined the effect of various types of antimicrobial treatment in controlling biofilm formation on devices. For example, the use of chlorohexidine/silver sulfadiazine in impregnating the surface of vascular catheters resulted in limited activity against gram-negative bacilli, such as *Pseudomonas*. Catheters impregnated with minocycline and rifampin were somewhat effective in preventing bacterial colonization (Darouiche et al., 1999). Anwar et al. (1992) showed that treatment with levels of tobramycin far in excess of the MIC reduced biofilm cell counts for *P. aeruginosa* by approximately 2 logs, while the same dosage provided a >8-log decrease in planktonic cells of this organism. Addition of sodium metabisulfite to a dextrose-heparin flush eliminated microbial colonization of atrial catheters (Freeman and Gould (1985). Catheters coated with a cationic surfactant (tridodecylmethylammonium chloride), which was in turn used to bond cephalosporin to the surface, were found less likely to become contaminated and develop biofilms than were untreated catheters (Kamal et al., 1991). Flowers et al. (1989) found that an attachable subcutaneous cuff containing silver ions inserted after local application of polyantibiotic ointment conferred a protective effect on catheters, resulting in lower rates of contamination. Maki (1994) suggested several ways to control biofilms on central venous catheters, including using aseptic technique during implantation, using topical antibiotics, minimizing the duration of catheterization, using an in-line filter for intravenous fluids, creating a mechanical barrier to prevent influx of organisms by attaching the catheter to a surgically implanted cuff, coating the inner lumen of the catheter with an antimicrobial agent, and removing the contaminated device.

Antiseptics used in industrial applications have also failed to prevent biofilm growth formation of bacterial organisms. For example, industrial water contamination and public health issues due to an outbreak of *P. aeruginosa* peritonitis was traced back to contaminated poloxamer-iodine solution, a disinfectant used to treat the peritoneal catheters. *P. aeruginosa* was found to contaminate distribution pipes and water filters used in plants that manufacture iodine solutions. Once the organism had matured into a biofilm, it became resistant to the biocidal activity of the iodophor solution. Hence, biofilm growth formation causes mechanical problems in industrial settings, which in some instances may lead to infections in humans.

Other methods of inhibiting biofilm formation in medical and industrial settings have previously been developed using metal chelators (U.S. Patent Application Ser. No. 60/373,461). These methods have disclosed the use of small molecule chelators, i.e., EDTA, EGTA, deferoxamine, detheylenetriamine penta-acetic acid and etidronate for the inhibition of biofilm. U.S. Pat. No. 6,267,979 discloses the use of metal chelators in combination with antifungal or antibiotic compositions for the prevention of biofouling in water treatment, pulp and paper manufacturing, and oil field water flooding. U.S. Pat. No. 6,086,921 discloses the use of thiol containing compounds in combination with heavy metals as biocides; and U.S. Pat. No. 5,688,516 discloses the use of non-glycopeptide antimicrobial agents in combination with divalent metal chelating agents for use in the treatment and preparation of medical indwelling devices.

Although the current methods used to control biofilm growth formation have been somewhat effective, biofilm growth formation continues to be problematic in a variety of setting such as medical and industrial environments. Therefore, better means of targeting biofilm growth formation are needed in the art.

SUMMARY OF THE INVENTION

The present invention overcomes the deficiencies in the art of preventing biofilm growth formation by bacterial organisms. Thus, the present invention provides devices such as medical, and industrial devices coated/impregnated with a gallium-containing composition at a concentration sufficient to inhibit biofilm growth formation on the device or device surface. In a particular embodiment, the present invention provides a method of preventing biofilm growth formation on a device comprising impregnating or coating the device or surface thereof with a gallium-containing composition at a concentration sufficient to inhibit biofilm growth formation.

The present invention embodies any medical device, such as an indwelling medical device, that may be a vehicle for biofilm growth formation and hence cause nosocomial infections such as nosocomial pneumonias which are often due to the use of mechanical ventilation apparati. Thus, in some embodiments of the present invention is provided ventilation devices coated/impregnated with a gallium-containing composition at a concentration sufficient to inhibit biofilm growth formation.

Formation of biofilms within endotracheal tubes play a role in the initiation of ventilator-associated pneumonia. Thus, in some embodiments of the present invention is provided endotracheal tubes coated/impregnated with a gallium-containing composition at a concentration sufficient to inhibit biofilm growth formation.

Vascular catheters are a primary contributor to nosocomial bloodstream infections due to biofilm growth formation. Thus, in some embodiments of the present invention is provided vascular catheters coated/impregnated with a gallium-containing composition at a concentration sufficient to inhibit biofilm growth formation. Vascular catheters may include a central nervous system catheter, an arterial line, a pulmonary artery catheter, peripherally inserted central catheter (PICC), or midline catheter. The central nervous system catheter may be a intraventricular shunt.

Another type of catheter that commonly contributes to nosocomial infections due to biofilm growth formation is a urinary catheter. Thus, in some embodiments of the present invention is provided urinary catheters coated/impregnated with a gallium-containing composition at a concentration sufficient to inhibit biofilm growth formation.

Biofilm growth formation may also occur on surgical devices. Therefore, in some embodiments of the present invention is provided surgical devices coated/impregnated with a gallium-containing composition at a concentration sufficient to inhibit biofilm growth formation.

The present invention further embodies other indwelling medical devices such as, but not limited to, epidural catheters, or peritoneal catheters coated with a gallium-containing composition at a concentration sufficient to inhibit biofilm growth formation. Other devices of the present invention may include, but are not limited to, an orthopedic device; a prosthetic device; a stent, such as a vascular stent, biliary stent, or a urinary stent; a guidewire; a nephrostomy tube; a pacemaker; a medical implant; an optical or ocular lens such as a contact lens; or a drainage tube. Other medical devices that can be coated/impregnated with the gallium-containing composition of the present invention include blood exchanging devices, vascular access ports, cardiovascular catheters, extracorpeal circuits, implantable prostheses, vascular grafts, pumps, heart valves, and cardiovascular sutures, to name a few.

In another embodiment of the present invention, the device may be a biological fluid delivery device or container such as, but not limited to a pre-filled syringe, IV bag, bottle, or ampule. In yet another embodiment, the device of the present invention may be a drug delivery device such as a patch. The patch may be a drug containing device, system, composition, bandage, or plaster. In still yet another embodiment of the invention, the device may be a coded device such as a computer chip.

In another particular embodiment of the present invention, there is provided a method of preventing biofilm growth formation on a medical device comprising impregnating/coating the device or surface thereof with a gallium-containing composition at a concentration sufficient to inhibit biofilm growth formation. Impregnating or coating may comprise immersing the medical device or device surface in the gallium-containing composition; drying the device or device surface; and rinsing the excess composition from the device or device surface.

In further particular embodiments, a gallium-containing composition of the present invention may be employed in non-medical applications for gallium's anti-biofilm actions. Biofouling by bacterial biofilms is a major problem in many settings such as dental equipment, heating and cooling apparatus, the food service and water treatment industries, and many others. Thus, in further embodiments of the present invention the device may be a dental device such as a dental implant, but is not limited to such, and may include other dental devices or equipment.

In still other embodiments, the present invention provides industrial devices coated/impregnated with a gallium-containing composition at a concentration sufficient to inhibiting biofilm growth formation on the device or surface thereof. The industrial device may include, but is not limited to, a food processing device, a food collecting, or a water containing apparatus. The water containing apparatus may be a swimming pool, tub, sink, storage tank, well, bottle, or spa. In still a further embodiment, the industrial device may be a water-processing device, a water-cooling device, a water injection jet device, or a paper and pulp manufacturing device.

In still yet another embodiment of the present invention, there is provided a method of preventing biofilm growth formation on an industrial device comprising impregnating/coating the device or surface thereof with a gallium-containing composition at a concentration sufficient to inhibit biofilm growth formation. Impregnating or coating may comprise immersing the industrial device or device surface in the gallium-containing composition; drying the device or device surface; and rinsing the excess composition from the device or device surface.

It is contemplated in the present invention that the gallium-containing composition could be applied to any vulnerable surface to prevent or inhibit biofilm growth formation. Such surfaces may include a countertop, table-top, floor, cutting board, wall, or ceiling.

In still a further embodiment, the present invention provides a kit for inhibiting or preventing biofilm growth formation comprising a gallium-containing composition.

The present invention contemplates that the gallium-containing composition described herein may be used to inhibit or prevent biofilm growth formation by a wide variety of organisms such as, for example gram-positive, or gram-negative bacteria. In particular embodiments, the biofilm growth formation may be caused by a *Pseudomonas* species such as *P. aeruoginosa*.

It is also contemplated that the gallium-containing composition of the present invention may be use to prevent biofilm formation in an animal model or in human subjects.

Since nosocomial bacterial infections due to biofilm growth formation may result in diseases such as bacteremia, pneumonia, meningitis, osteomyelitis, endocarditis, sinusitis, arthritis, urinary tract infections, tetanus, gangrene, colitis, acute gastroenteritis, bronchitis, and a variety of abscesses, and opportunistic infections, the present invention further contemplates a method of preventing such diseases comprising providing an effective amount of a gallium-containing composition to a subject in need thereof.

Biofilm formation caused by *P. aeruginosa* has been evident in cystic fibrosis lung infection. Thus, in a further embodiment, the present invention contemplates a method of preventing biofilm growth formation in a subject having cystic fibrosis comprising providing to the subject a therapeutically effective amount of a gallium composition. The gallium-containing composition of the present invention may be delivered systemically, by aerosol, topically, or by any means known in the art for delivery or administration of a therapeutic agent to a subject.

The gallium-containing composition of the present invention may also be applicable to the prevention of biofilm growth formation caused by *P. aeruginosa* infections at sites other than the lung. For example, burn wounds often become infected with *P. aeruginosa* from which life-threatening invasion of the blood stream and septic shock can arise. These infections are felt to involve the formation of biofilms. Thus, topical application of the gallium-containing composition of the present invention to the wounds could prevent the initiation of infection by preventing or inhibiting biofilm growth formation.

In a further embodiment of the present invention, there is provided a method of killing an established biofilm on a device comprising exposing the device to a gallium-containing composition at a concentration sufficient to kill the established biofilm. In another embodiment, there is provided a method of killing an established biofilm on a surface comprising exposing the surface to a gallium-containing composition at a concentration sufficient to kill the established biofilm.

In still a further embodiment, the present invention provides a kit for killing an established biofilm comprising a gallium-containing composition.

The term "medical indwelling device" refers to any medical device implanted or inserted in the human body. Such devices can be temporarily or permanently implanted or inserted.

Thus, the present invention may have use in a variety of applications such as, but not limited to, industrial applications, medical applications, and public health applications. Regardless of detailed embodiments, applicability of the invention is not meant to be limiting.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A, 1B, 1E and 1F are top view (x-y plane); scale bar, 10 μm. FIGS. 1C, 1D, 1G and 1H are side views (x-z plane); scale bar, 50 μm. Results are representative of six experiments.

(FIG. 3A) Erdman *M. tuberculosis* ($10^6$/ml) was incubated in 7H9 medium without added OADC and Fe in the presence of the indicated concentrations of $Ga(NO_3)_3$. At defined time points aliquots of bacterial suspensions were inoculated into duplicate BACTEC 12B bottles, and the subsequent growth index was determined. The cumulative data for the indicated concentrations of $Ga(NO_3)_3$ at 24, 48, and 72 h are shown and represent the mean±SEM of three independent experiments. (FIG. 3B) Erdman *M. tuberculosis* ($10^6$/ml) was incubated in 7H9 medium without added ODAC and Ga, to which was added 10 μM $Ga(NO_3)_3$ and increasing concentrations of Fe-citrate. At 72 h bacterial suspensions were inoculated into BACTEC 12B bottles, and the subsequent growth index was determined. The results shown (mean±SD) are from a representative experiment (n=2). Fe was also found to reverse the growth-inhibitory effect of $Ga(NO_3)_3$ on Erdman *M. tuberculosis* and MAC when the experiments were performed in BACTEC bottles (high-Fe-containing medium) (data not shown).

In FIG. 5B, cumulative data are expressed as the percentage of the control (mean±SEM, n=2 to 5). Results using HAMs (n=2) were the same as those using MDMs.

FIGS. 10A-10D show that gallium kills established biofilms in a time and concentration dependent manner, and it does so at concentrations within peak levels achieved clinically (140-700 μM).

DESCRIPTION OF ILLUSTRATIVE EMBODIMENTS

I. The Present Invention

Figures 1A, 1B, 1C, 1D, 1E, 1F, 1G, 1H:
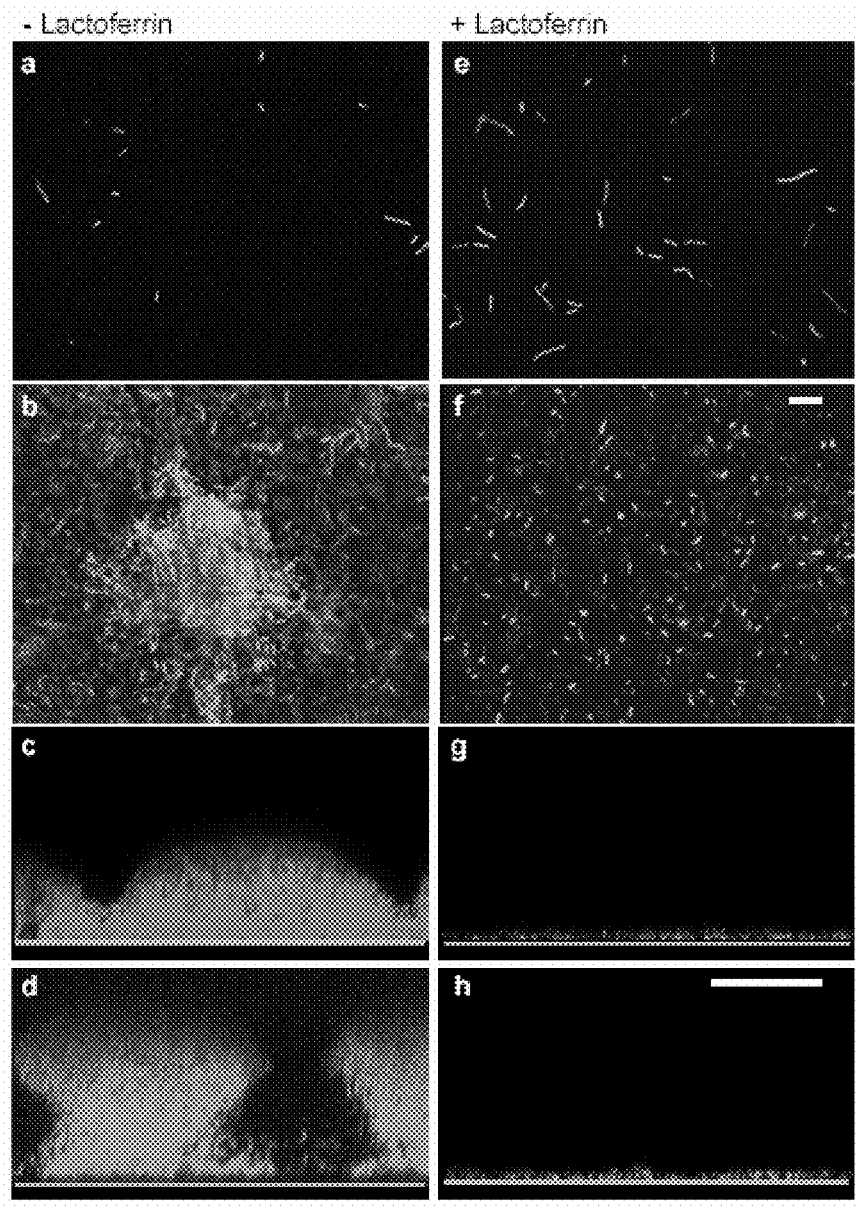
FIGS. 1A-1H. Confocal microscopic images of GFP-labeled *P. aeruginosa* in biofilm flow cells perfused with lactoferrin-free (FIGS. 1A-1D) and lactoferrin-containing (20 μg ml) (FIGS. 1D-1H) media. Images were obtained 4 h (FIGS. 1A and 1E), 24 h (FIGS. 1B-1F), 3 days (FIGS. 1C-1G) and 7 days (FIGS. 1D-1H) after inoculating the flow cells.

The present invention overcomes the deficiency in the art in preventing biofilm growth formation. Bacteria within biofilms have been found to be intrinsically more resistant to killing by antibiotics and other exogenous toxins such as hydrogen peroxide (Costerton et al., 1999; Stewart et al., 2000; Elkins et al., 1999; Drenkard et al., 2002; Mah et al., 2001) than planktonic cells because of the diminished rates of mass transport of antimicrobial molecules to the biofilm associated cells (Suci et al., 1994) or because biofilm cells differ physiologically from planktonic cells (Evans et al., 1991). Antimicrobial concentrations sufficient to inactivate planktonic organisms are generally inadequate to inactivate biofilm organisms, especially those deep within the biofilm, potentially selecting for resistant subpopulations. Biofilm growth formation also make it difficult for host phagocytic cells to gain access to and kill the organisms. Thus, developing agents that prevent and/or disrupt biofilm formation caused by organisms such as P. aeruginosa are needed.

The inventors have shown that iron (Fe) availability is critical at several steps in the pathogenesis of infection with P. aeruginosa which leads to the formation of biofilms by these organisms. Gallium (Ga), is able to compete with Fe for cellular uptake and substitution of gallium for Fe in Fe-containing enzymes renders them inactive. Substantial data generated by the inventors also demonstrate that gallium is capable of disrupting the siderophore-mediated Fe acquisition strategy of M. tuberculosis, a strategy with many similarities to that employed by P. aeruginosa. Preliminary data obtained was consistent with a similar inhibitory effect of gallium on the growth of P. aeruginosa. Most importantly, the data indicates that gallium effectively prevents the formation of biofilms in vitro by P. aeruginosa at concentrations that do not inhibit bacterial growth and which are well below those which are known to be achievable in humans administered gallium for other purposes. The data suggest that gallium can disrupt the Fe metabolism of P. aeruginosa, thereby altering key steps in the establishment of biofilms by this organism.

The inventors have also shown that gallium effectively kills established biofilms in a time and concentration dependent manner, and it does so at concentrations within peak levels achieved clinically.

Thus, the present invention provides devices or surfaces thereof coated/impregnated with a gallium-containing composition to prevent or inhibit biofilm growth formation. The present invention also provides a method for preventing biofilm growth formation on a device or surface thereof. In preferred embodiments, the gallium-containing composition is utilized to prevent P. aeruginosa biofilm formation on devices such as endotracheal tubes, ventilators, other medical devices, or industrial devices by coating/impregnating the device with the composition. It is also contemplated that the gallium-containing composition of the present invention may be used in preventing biofilms formed by other organisms that are similarly Fe-dependent as P. aeruginosa. The gallium-containing composition of the present invention may also be employed in preventing biofilm growth formation in a subject such as cystic fibrosis patients and other P. aeruginosa infected patients. Further, the gallium-containing composition of the present invention may be used to kill established biofilms on a device or surface.

II. Bacterial Organisms and Biofilm Formation

Biofilm growth formation occurs when microorganisms irreversibly adhere to a submerged surface and produce extracellular polymers that facilitate adhesion and provide a structural matrix. This surface may be inert, nonliving material or living tissue. Biofilm-associated microorganisms behave differently from planktonic (freely suspended) organisms with respect to growth rates. Additionally, biofilms are characterized by their ability to become increasingly resistance to antimicrobial treatments (1000- to 1500-fold less susceptible). In some instances, biofilms may be composed of single species or multiple species, depending on the device and its duration of use in, or by, a patient.

Resistance of biofilms to antimicrobial agents is believe to be due to the extracellular matrix in which the bacterial cells are embedded providing a barrier toward penetration by the biocides (Costerton et al., 1999). However, it is also possible that a majority of the cells in a biofilm are in a slow-growing, nutrient-starved state, and therefore not as susceptible to the effects of anti-microbial agents. Additionally, the resistance to antimicrobial agents may be due to the cells in a biofilm adopting a distinct and protected biofilm phenotype, e.g., by elevated expression of drug-efflux pumps.

Biofilms can be comprised of bacteria, fungi, yeast, protozoa, and other microorganisms. The most common biofilms have been found to be bacterial biofilms. Both gram negative and gram positive bacteria are capable of forming biofilms. Examples of gram positive bacteria that are capable of forming biofilms including, but not limited to, *Staphylococcus aureus*, coagulase negative staphylocci such as *Staphylococcus epidermis, Streptococcus pyogenes* (group A), *Streptococcus* species (viridans group), *Streptococcus agalactiae* (group B), *S. bovis, Streptococcus* (anaerobic species), *Streptococcus pneumoniae*, and *Enterococcus* species. Other gram-positive bacilli include *Bacillus anthracis, Corynebacterium diphtheriae* and *Corynebacterium* species which are diptheroids (aerobic and anerobic), *Listeria monocytogenes, Clostridium tetani*, and *Clostridium difficile*. Examples of gram negative bacteria that are capable of forming biofilms are bacteria from the genus *Escherichia coli, Enterobacter* species, *Proteus mirablis* and other species, *Pseudomonas aeruginosa, Klebsiella pneumoniae, Salmonella, Shigella, Serratia*, and *Campylobacter jejuni, Neisseria* and *Branhamella catarrhalis*.

Additional organisms capable of forming biofilm may include dermatophytes (*Microsporum canis* and other M spp.; and *Trichophyton* spp. such as *T. rubrum*, and *T. mentagrophytes*), yeasts (e.g., *Candida albicans, C. Parapsilosis, C. glabrata, C. tropicalis*, or other *Candida* species including drug resistant *Candida* species), *Epidermophyton-floccosum, Malassezia fuurfur* (*Pityropsporon orbiculare*, or *P. ovate*), *Cryptococcus neoformans, Aspergillus fumigatus*, and other *Aspergillus* spp., *Zygomycetes* (*Rhizopus, Mucor*), *hyalohyphomycosis* (*Fusarium* Spp.), *Paracoccidioides brasiliensis, Blastomyces dermatitides, Histoplasma capsulatum, Coccidioides immitis*, and *Sporothrix schenckii*.

The organisms causing biofilm growth formation that are most commonly isolated from indwelling devices include *Staphylococcus* species such as *S. epidermidis* and *S. aureus; Candida* species such as *Candida albicans*; enterococci species such as *Enterococcus faecalis, Streptococcus* species; *P. aeruginosa; K pneumoniae*; and diphtheroids. These organisms may originate from the skin of patients or healthcare workers, tap water to which entry ports are exposed, or other sources in the environment, specifically a healthcare facility.

The predilection of *Pseudomonas aeruginosa* to form biofilms is a major contributing factor to the problems of biofilm growth formation in the medical and industrial environments. *P. aeruginosa* is highly associated with biofilm growth and catheter obstruction. For example, biofilms of *P. aeruginosa* have been isolated from medical implants, such as indwelling urethral, venous or peritoneal catheters (Stickler et al., 1998).

*P. aeruginosa* is also the most common cause of pneumonia in patients undergoing mechanical ventilation (Lode et al., 1992; Adair et al., 1999), and this is among the most devastating infections affecting the critically ill (Chastre et al., 2002; Bergmans et al., 1998). Recent work indicates that a key factor in the development of ventilator-associated pneumonia is colonization of the endotracheal tube and oropharynx by bacteria living in biofilms (Inglis et al., 1989; Koerner, 1997; Levine et al., 1991; Sottile et al., 1986; Bauer et al., 2002). *P. aeruginosa* is also a cause of community-acquired pneumonia in patients in the advanced stages of AIDS (Shepp et al., 1994; Schuster et al., 1994). These patients frequently become susceptible to infections due to biofilm growth formation from bacteria (Meynard et al., 1999).

In addition to these acute infections, *P. aeruginosa* causes chronic infections of the lung in patients with cystic fibrosis (CF) or chronic bronchiectasis (Fick et al., 1989; Marshall et al., 1991; Pollack et al., 2000) which are due to biofilm growth formation (Costerton et al., 1999). Lung injury, associated with persistent *P. aeruginose* infection, is currently the primary cause of death in CF (Fick et al., 1989).

Thus, in a further embodiment, the present invention contemplates a method of preventing biofilm growth formation in a subject having cystic fibrosis comprising providing to the subject a therapeutically effective amount of a gallium composition. The gallium-containing composition of the present invention may be delivered systemically, by aerosol, topically, or by any means known in the art for delivery or administration of a therapeutic agent to a subject.

The gallium-containing composition of the present invention may also be applicable to the prevention of *P. aeruginosa* infections at sites other than the lung. For example, burn wounds often become infected with *P. aeruginosa* from which life-threatening invasion of the blood stream and septic shock can arise. These infections are felt to involve the formation of biofilms. Thus, topical application to the wounds of the gallium-containing composition of the present invention could prevent the initiation of infection by preventing or inhibiting biofilm formation.

Biofilms such as *P. aeruginosa* also pose a problem of industrial concern (Bitton, 1994; Steelhammer et al., 1995). This organism grows in an aggregated state, the biofilm, which causes problems in many water-processing plants.

III. Gallium-Containing Compositions and Uses Thereof

Gallium is a group IIIa transition metal that has been used in nuclear medicine as a means for localizing neoplasms and inflammatory sites. Gallium localizes to these sites because of the predilection of gallium for certain neoplastic and inflammatory cells. The biological and therapeutic effects of $Ga^{3+}$ appear to relate to its ability to substitute for $Fe^{3+}$ in many biomolecular processes, thereby disrupting them (Chitambar et al., 1988; Hubbard et al., 1986). $Ga^{3+}$, like $Fe^{3+}$, enters mammalian cells, including macrophages, via both transferrin-dependent and transferrin-independent Fe uptake mechanisms (Chitambar et al., 1987; Olakanmi et al., 1994). In rapidly dividing tumor cells (as opposed to terminally differentiated cells such as macrophages), gallium interferes with cellular DNA replication via its ability to substitute for iron in ribonucleotide reductase, resulting in enzyme inactivation due to the fact that gallium, unlike iron, is unable to undergo redox cycling (Chitambar et al., 1988).

Gallium has also been used therapeutically for malignant neoplasms and malignancy-associated hypercalcemia (Foster, et al., 1986; Todd et al., 1991; Jonkoff et al., 1993; Chitambar et al., 2003). It is also known that gallium can accumulate in cells of mononuclear origin in the liver, kidney, spleen and lymphatic system. Clinical experience in patients with cancer-related hypercalcemia indicates that gallium nitrate is well tolerated, producing few clinically relevant adverse effects (Todd, et al., 1991; Leyland-Jones, 1991; Chitambar et al., 2003). Gallium, in the form of $Ga(NO_3)_3$, is currently approved for intravenous administration in humans for the treatment of hypercalcemia of malignancy. An oral formulation of gallium, in the form of gallium maltolate, is currently in clinical trials for the treatment of metastatic prostate cancer, refractory multiple myeloma, metastatic bladder cancer and refractory lymphoma. This drug is being developed by Titan Pharmaceutical (San Francisco, Calif.).

Gallium-containing compounds and gallium nitrate have also been shown to inhibit intracellular pathogens that cause chronic pulmonary infections (for example, see WO 98/09622, U.S. Pat. Nos. 5,997,912, and 6,203,822) each incorporated herein by reference in their entirety.

The present invention provides a gallium-containing composition at a concentration effective to inhibit or prevent biofilm growth formation. The amount of gallium required to inhibit biofilm growth formation is less than that required to kill or inhibit the bacterial organism. Thus, in some embodiments, the concentration of the gallium may be at least about 1, 2, 3, 4, 5, 6, 7, 8, 9, 10, 11, 12, 13, 14, 15, 16, 17, 18, 19, 20 µM or greater. In further embodiments of the present invention, the gallium concentration may be about 1 µM to about 10 µM, about 2 µM to about 15 µM, about 4 µM to about 12 µM, about 5 µM to about 20 µM, about 10 µM to about 30 µM, about 15 µM to about 40 µM, about 20 µM to about 50 µM, or greater. In some preferred embodiments the gallium concentration may be about 16.25 µM to about 100 µM. The gallium concentration of the present invention may depend on the amount of iron available in the composition given that gallium has the ability to substitute for iron. One of ordinary skill in the art would know how to determine the gallium concentration based on the iron availability.

The present invention further provides a gallium-containing composition at a concentration effective to kill established biofilms. In some embodiments, the concentration of the gallium may be about 10 µM to about 1000 µM. In further embodiments of the present invention, the gallium concentration may be about 140 µM to about 700 µM. In other embodiments, the gallium concentration may be about 10 µM to about 100 µM. In other embodiments, the gallium concentration may be about 100 µM to about 1000 µM. The gallium concentration of the present invention may depend on the amount of iron available in the composition given that gallium has the ability to substitute for iron. One of ordinary skill in the art would know how to determine the gallium concentration based on the iron availability.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Fe Availability and *P. aeruginosa* Biofilm Growth Formation

It is well known in the art that *P. aeruginosa* forms biofilms via a carefully regulated process. Biofilm formation has been shown it to be regulated by the *P. aeruginosa* quorum sensing system (Davis et al., 1998). Previous work by the inventors demonstrated that Fe availability plays a critical role in the establishment phase of a biofilm by *P. aeruginosa*. Additionally, the inventors have shown that gallium can disrupt bacterial Fe-dependent metabolism. Gallium, at sub-inhibitory concentrations was found to prevent biofilm formation by *P. aeruginosa* in vitro.

Figures 2A, 2B:
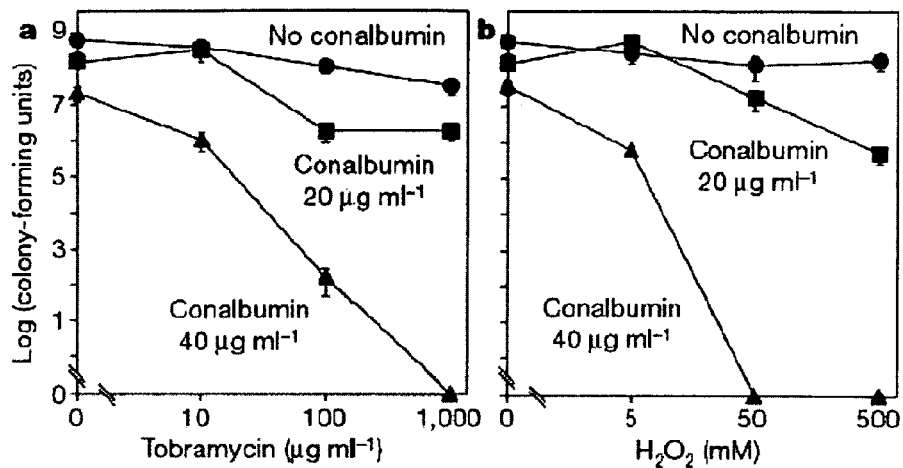
FIGS. 2A-2B. Effect of conalbumin on the antimicrobial susceptibility of *P. aeruginosa* biofilms to tobramycin (FIG. 2A) and $H_2O_2$ (FIG. 2B). Data are mean±SEM, n=6 from three different experiments.

Preliminary studies demonstrated that concentrations of the Fe-binding protein lactoferrin (LF) that did not alter *P. aeruginosa* growth profoundly inhibited biofilm formation by *P. aeruginosa* as determined microscopically in a previously developed flow cell model of biofilm formation (Singh et al., 2002; FIGS. 1A-1H). This effect was reversed by the presence of Fe and duplicated, as shown in FIGS. 2A-2B, using the Fe chelators deferoxamine or conalbumin (Singh et al., 2002). The results lead to the conclusion that *P. aeruginosa* biofilm formation was more sensitive to environmental Fe levels than was bacterial growth.

Fe limitation also lead to an increased susceptibility of *P. aeruginosa* to killing by tobramycin or $H_2O_2$ (Singh et al., 2002; FIGS. 2A-2B), most likely because the LF disrupted biofilm formation. Once the biofilm was established, however, LF was unable to alter the biofilm. Additional work demonstrated that the effect of Fe limitation on biofilm formation correlated with an alteration in *P. aeruginosa* motility—low Fe availability stimulated twitching motility, which presumably serves to prevent the organism from progressing from a planktonic state to the initiation of a biofilm (Singh et al., 2002).

These data suggest that factors other than Fe chelators that alter the availability of Fe for use by *P. aeruginosa*, or disrupt its signaling systems in such a way that it believes that it is in an Fe-limited environment, will result in a decreased predilection of the organism to form a biofilm.

Example 2

Antimicrobial Activity of Gallium Against Pathogenic *Mycobacteria*

Figures 3A, 3B:
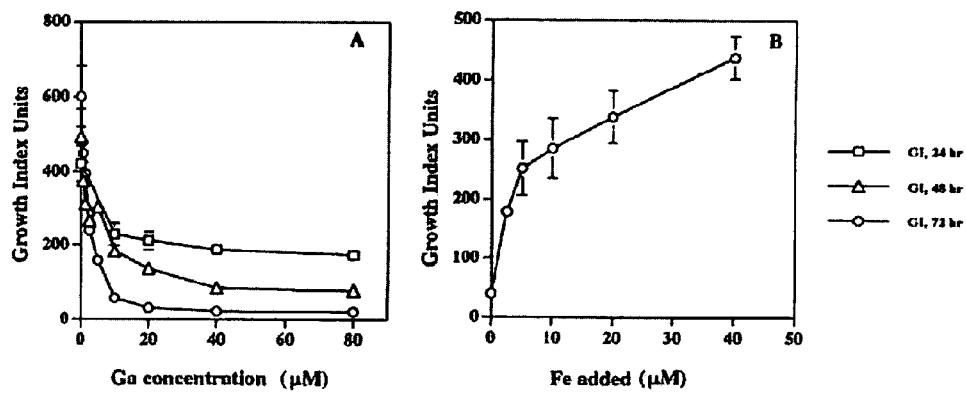
FIGS. 3A-3B. Low concentrations of $Ga(NO_3)_3$ inhibit the growth of *M. tuberculosis* under physiologic Fe conditions; the inhibition of growth is prevented in the presence of excess Fe.

The inventors have previously shown that gallium inhibits the growth of *M. tuberculosis* and *Mycobacterium Avium* Complex (MAC) extracellularly and within human macrophages (Olakanmi et al., 2000). *Mycobacteria* were incubated in BACTEC 12B broth culture bottles in the absence or presence of $Ga(NO_3)_3$. The BACTEC system monitors mycobacterial growth as release of $^{14}CO_2$ generated during bacterial incorporation of [$^{14}C$] palmitate into the mycobacterial cell wall. A concentration-dependent growth inhibition of each mycobacterial strain was observed with $Ga(NO_3)_3$ (Olakanmi et al., 2000). The BACTEC system was employed because of its sensitivity and speed. However, its medium contains up to 1.6 mM Fe (ferrozine assay). In comparison, the concentration of extracellular Fe in vivo is 5-10 µM. When Erdman *M. tuberculosis* was exposed to gallium in 7H9 broth made without Fe supplementation (2 µM Fe), as expected, significant growth inhibition of *M. tuberculosis* was seen at much lower gallium concentrations (FIG. 3A). The $IC_{50}$ was approximately 1.25-2.5 µM at 72 h of gallium exposure. Gallium-mediated growth inhibition was reversed at $Fe^{3+}$ concentrations ≥$Ga^{3+}$ concentrations (FIG. 3B).

Figures 4A, 4B:
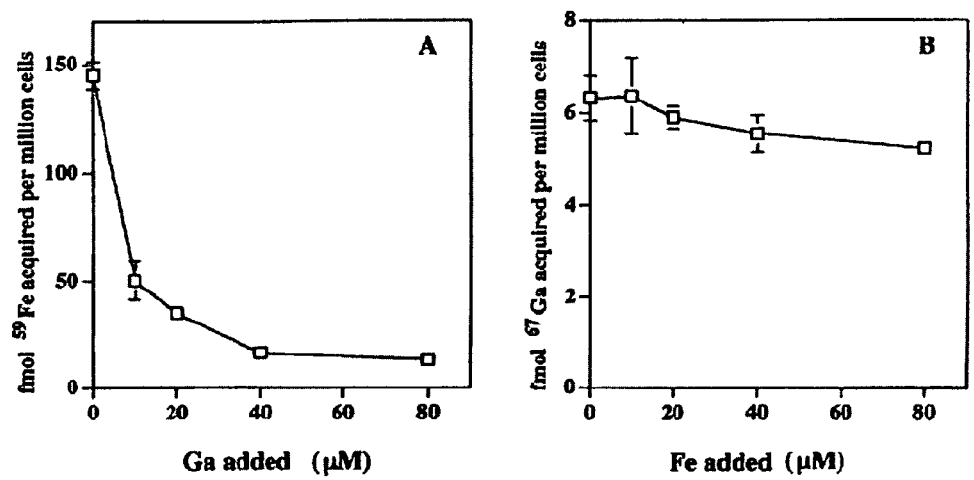
FIGS. 4A-4B. Fe uptake by *M. tuberculosis* is markedly inhibited in the presence of gallium, whereas gallium uptake is inhibited to only a small degree by excess Fe. Erdman *M. tuberculosis* ($2 \times 10^7$ ml) was incubated for 6 h in 7H9 medium (without added Fe and OADC) with 500 nM $^{59}$Fe-citrate (FIG. 4A) or $^{67}$Ga-citrate (FIG. 4B) in the absence or presence of the indicated concentrations of cold competing metal. The bacteria were then washed repeatedly, and bacterium-associated $^{67}$Ga or $^{59}$Fe levels were determined. Results are shown as the amount of metal acquired as a function of increasing concentrations of the cold competing metal. Experimental groups were performed in triplicate, and the data shown represent three independent experiments (mean±SEM).

These data suggest that gallium mediates its antimicrobial effects in part by disrupting mycobacterial Fe acquisition. Surprisingly, as assessed using $^{67}Ga$ or $^{59}Fe$, the bacteria appear to have a greater capacity for Fe than Ga accumulation. Finally, whereas gallium was highly effective in competing for the *M. tuberculosis* acquisition of $^{59}Fe$, Fe was relatively ineffective in blocking $^{67}Ga$ acquisition (FIG. 4; Olakanmi et al., 2000).

Example 3

Figures 5A, 5B:
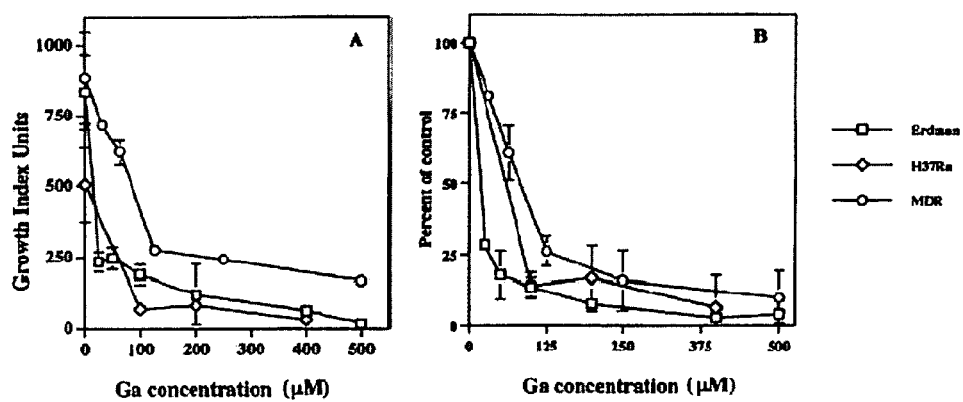
FIGS. 5A-5B. Ga(NO$_3$)$_3$ inhibits the growth of M. tuberculosis within human macrophages in a concentration-dependent manner. Mycobacteria (Erdman, H37Ra, and MDR M. tuberculosis) were added to human monocyte-derived macrophages (MDM) or human alveolar macrophages (HAM) monolayers at multiplicities (bacterium/macrophage) ranging from 1:1 to 5:1 (the results were the same). After 2 h, the monolayers were washed, and repletion medium was added. The indicated concentrations of Ga(NO$_3$)$_3$ were added 24 h later. Control monolayers were devoid of Ga(NO$_3$)$_3$. Growth index readings of combined supernatants and cell lysates from duplicate or triplicate wells were recorded on day 3 with the indicated concentrations of Ga(NO$_3$)$_3$. Shown in FIG. 5A is a representative experiment using MDMs (mean±SD).

Antimicrobial Activity of Gallium Against Pathogenic *Mycobacteria* within Macrophages The critical site of growth of mycobacteria in vivo is within host macrophages. Gas is found to inhibit *M. tuberculosis* growth within these cells (Olakanmi et al., 2000; FIG. 5A). $NaNO_3$ had no effect on mycobacterial growth, confirming that gallium was responsible. Although mycobacterial growth was inhibited up to 50% at 24 hr, more striking inhibition (>70%) was observed after 48 hrs (FIG. 5B). This may relate to the time required for uptake and trafficking of gallium into the macrophage and then to the bacterium. The effect of gallium was not due to loss of the monocyte-derived macrophage (MDM) monolayer. In fact, gallium prevented loss of monolayers over time due to *M. tuberculosis* multiplication.

When $Ga(NO_3)_3$ is administered intravenously, a majority of the gallium is chelated by serum transferrin (TF) (Seligman et al., 1992; Bernstein, 1998). Ga-TF was found to be as effective as $Ga(NO_3)_3$ in inhibiting mycobacterial growth in both liquid media and within human macrophages (Olakanmi et al., 2000). Gallium was bactericidal for *M. tuberculosis* extracellularly and even more so when the bacteria were growing intracellularly in macrophages (Olakanmi et al., 2000).

Example 4

Gallium Decreases Fe Acquisition by Intracellular *M. tuberculosis*

Figure 6:
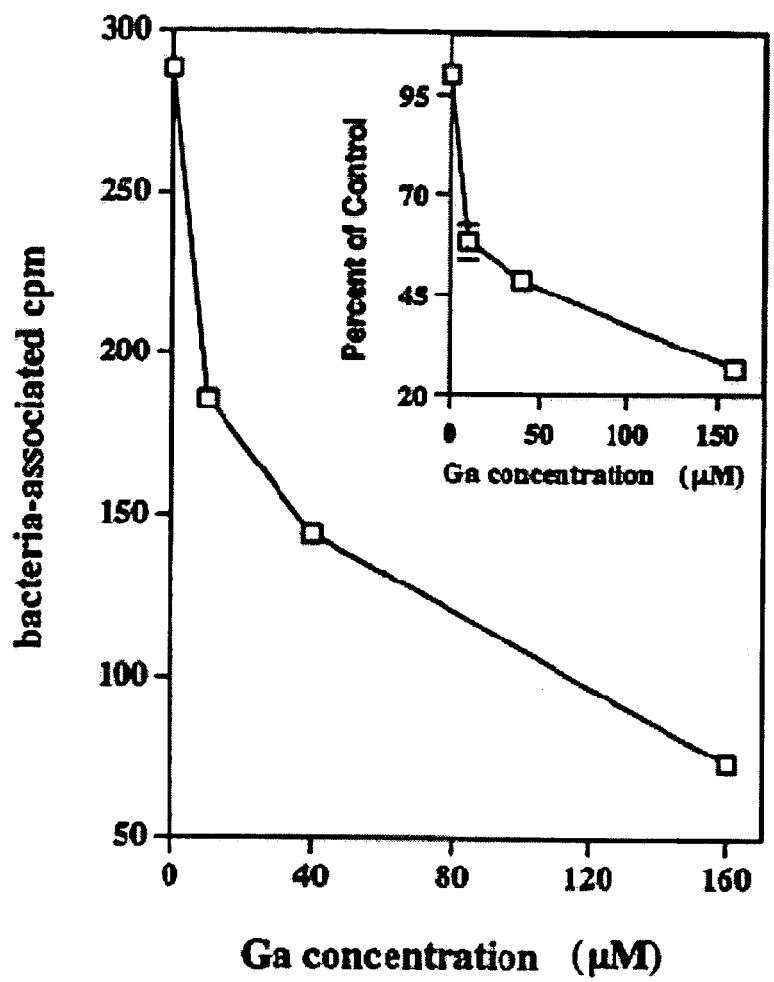
FIG. 6. Ga-transferrin inhibits Fe acquisition by M. tuberculosis within macrophage phagosomes in a concentration-dependent manner. $^{59}$Fe transferrin (10 μM) was added to M. tuberculosis-containing MDMs in the absence (control) or the presence of the indicated concentrations of Ga-transferrin for 24 h MDMs were lysed, and the lysates were filtered through a 0.22-μm (pore-size) filter. M. tuberculosis-associated radioactivity (expressed in cpm) on the filter was determined. Shown are the cpm values as a function of the Ga concentration added from a representative experiment. The inset shows the mean±SEM results of three separate experiments plotted as the percentage of control $^{59}$Fe acquisition.

Fe-TF is the major form of extracellular Fe, and transport of exogenously added TF to the *M. tuberculosis*-containing phagosome of human macrophages (Clemens et al., 1996) has been observed. It was therefore hypothesized that gallium competes with Fe uptake by bacteria dividing within the phagosome. The inventors used an assay developed in their laboratory, to show that *M. tuberculosis* located within a macrophage phagosome acquire extracellular $^{59}Fe$ bound to TF (Olakanmi et al., 2000). However, the presence of 10 µM $Ga(NO_3)_3$ markedly decreased $^{59}Fe$ acquisition by intraphagosomal *M. tuberculosis* (FIG. 6; Olakanmi et al., 2000). This was not due to differences in total MDM $^{59}Fe$.

In two recent preliminary experiments, MDM monolayers were preloaded with either $^{59}Fe$ or $^{67}Ga$ or both (pulse/chase, 24 h each). Erdman *M. tuberculosis* was then added. After 48 h, bacteria isolated from the phagosome were assessed for associated iron or gallium. Each metal could be found specifically associated with the bacteria. When gallium and iron were both added, iron acquisition was inhibited by 71% and 67% (n=2); in contrast, gallium acquisition was variably increased (52% and 22%).

Example 5

Effect of Gallium on the Fe Repressor Regulator Protein IdeR

The iron regulatory element, IdeR, regulates the production of catalase, SOD, and siderophores in mycobacteria (Dussurget et al., 1996) in a manner analogous to *P. aeruginosa* Fur. In order for DNA binding to occur, IdeR must be complexed with a divalent metal such as $Fe^{2+}$ or $Ni^{2+}$. The effect of $Ga(NO_3)_3$ on the binding (gel mobility shift assay) of IdeR was examined using the HisE promoter region from *M. tuberculosis* that contains a high affinity IdeR binding site (Schmitt et al., 1995). Gallium (200 µM) did not lead to IdeR binding to this DNA fragment, whereas binding was observed with 200 µM $Ni^{2+}$. Gallium did not interfere with $Ni^{2+}$ or $Fe^{2+}$ activation of IdeR binding. IdeR does not appear to be a target for gallium, which is not surprising given that the IdeR selectively binds divalent metals and gallium is trivalent (Schmitt et al., 1995). A similar lack of binding of $Ga^{3+}$ to *P. aeruginosa* Fur is expected based on these findings.

Example 6

Gallium Inhibits *M. tuberculosis* Ribonucleotide Reductase Activity

Next it was hypothesized that internalization of gallium by the bacterium could lead to disruption of Fe-dependent metabolic activity such as ribonucleotide reductase (RR). Consistent with this, other investigators have found gallium to be a potent inhibitor of RR activity; a radiolabeled CDP reduction assay for RR activity and *M. tuberculosis* RR, a type II RR (Yang et al., 1994; 1997) were used. 450 µM gallium inhibited RR activity by 50% (n=2), suggesting that gallium may inhibit the enzyme by directly displacing Fe from the enzyme's active site. The potency of gallium in this assay is 10-fold greater than hydroxyurea ($IC_{50}$=3-5 mM), a standard agent used experimentally to inhibit RR (Yang et al., 1997). As noted earlier, *P. aeruginosa* has been reported to be much more susceptible to inhibition of its growth and DNA production by hydroxyurea than other bacterial species (Gale et al., 1964). Although there is no data on the $IC_{50}$ of gallium for purified mammalian RR, it has been reported that 16 mM gallium (approximately 35 fold higher than $IC_{50}$ of gallium for *M. tuberculosis* RR) was required to decrease the characteristic EPR peak of the RR tyrosyl radical by 50% in a cell free extract of mammalian L1210 cells (Narasimhan et al., 1992). The concentration of gallium required to inhibit RR in the context of intact bacteria may be much less than that required to inhibit the purified enzyme used in these studies.

Example 7

Effect of Gallium on Growth of *P. aeruginosa*

Figure 7:
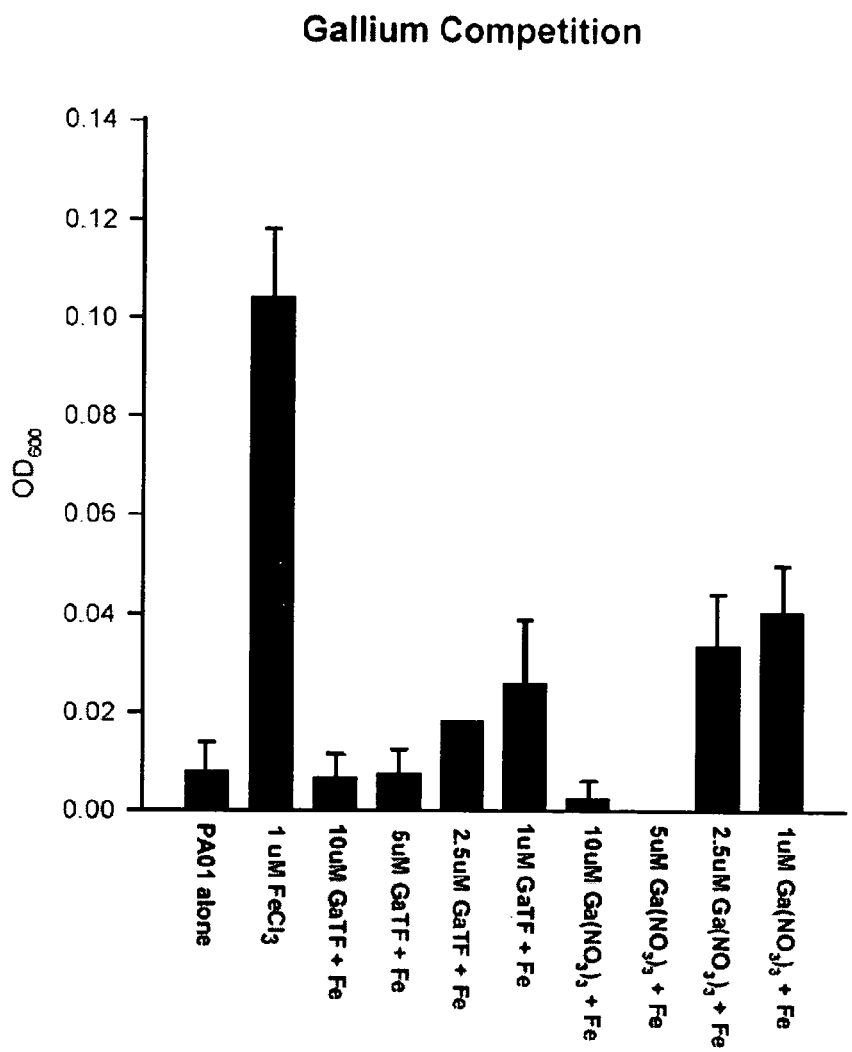
FIG. 7. P. aeruginosa was inoculated to an OD (A600) of about 0.010 into succinate media alone or with FeCl$_3$ supplementation +/− the Ga chelates. Growth was then monitored as the change in A600 over 6 h of incubation at 37° C. Longer incubations using Ga(NO$_3$)$_3$ showed a similar effect (data not shown).

The above data suggesting that gallium efficiently disrupts mycobacterial iron metabolism prompted the examination of the potential impact of gallium on the iron metabolism of *P.* aeruginosa grown in succinate media. P. aeruginosa growth is dependent on the addition of exogenous Fe (FIG. 7). Inclusion of 1 μM FeCl₃, to succinate media P. aeruginosa strain PA01 resulted in a >10-fold increase in P. aeruginosa concentration (A600) over 6 h, whereas a negligible increase was seen in the absence of the added iron. When gallium, either in the form of Ga(NO₃)₃ or Ga-TF, was added to iron-supplemented succinate media at concentrations ≥1 μM, a gallium concentration-dependent inhibition of P. aeruginosa growth was observed (FIG. 7). 100 nM gallium did not inhibit growth (not shown). Similar results were observed under different conditions (see below).

Example 8

Gallium Inhibits P. aeruginosa Biofilm Formation

The data indicated that iron chelation by lactoferrin inhibits P. aeruginosa biofilm development and that gallium can disrupt microbial iron acquisition. These results suggested that gallium may have anti-biofilm actions. Therefore, administering gallium to block biofilm formation provides a potential therapeutic approach given that effective iron chelation in vivo is likely to be very difficult for a number of reasons.

First, many pathogenic bacteria possess highly efficient iron acquisition mechanisms. Therefore an effective chelator would have to bind iron with an extremely high affinity. Second, bio-available iron is already very limited by host iron binding proteins present in extracellular fluids. This makes it unlikely that pharmaceutical chelators could reduce available iron much further. Third, pathogenic organisms like P. aeruginosa produce enzymes that can degrade iron chelators. Lastly, human cells require iron for many physiological processes. Thus, even if effective iron limitation were possible, this could have adverse effects on the host.

Figure 8:
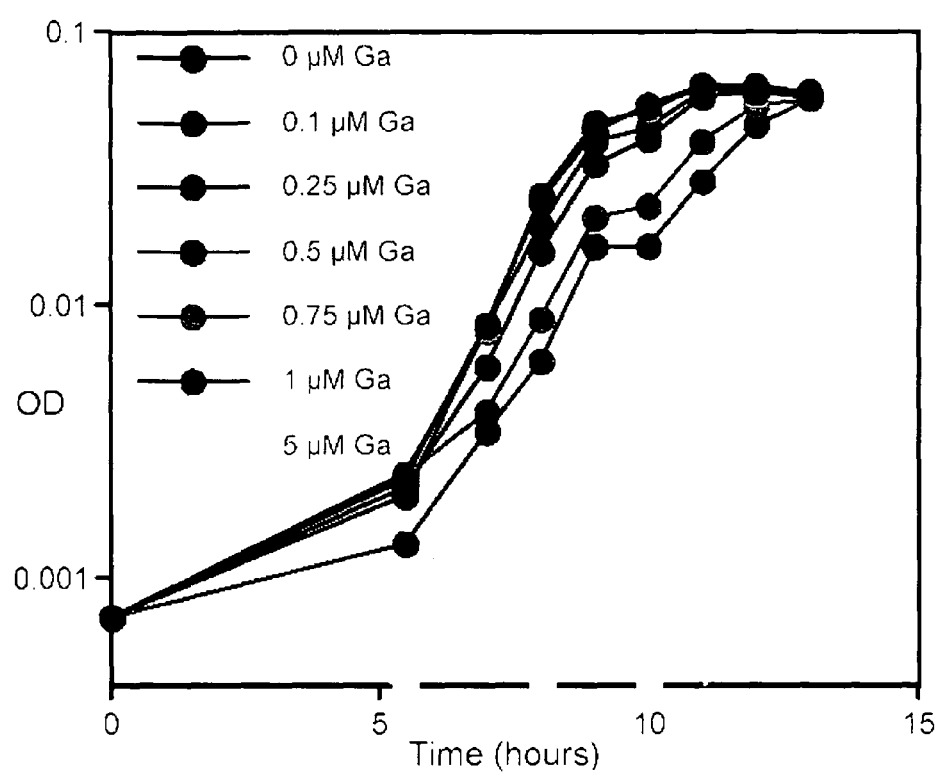
FIG. 8. Effect of gallium on the growth of P. aeruginosa. Bacteria were inoculated in 1:100 strength TSB medium with the indicated concentrations of gallium and grown at 37° C. with shaking. Growth was monitored as the change in A600 over 15 h.

To investigate the possibility that gallium inhibits biofilm development, sub-inhibitory concentration of Ga(NO₃)₃ (did not impair the growth of P. aeruginosa in the medium used in biofilm experiments, 1:100 strength TSB) were determined. This was important to assess the specific anti-biofilm actions of gallium and not effects that involve growth inhibition. As shown in FIG. 8, Ga(NO₃)₃ did not significantly decrease the growth rate of P. aeruginosa (in batch culture) until concentrations exceeded 1 μM.

In initial biofilm experiments, Ga(NO₃)₃ at a concentration of 0.3 μM, which was 3-fold lower than the inhibitory concentration for P. aeruginosa in this medium, was used. To evaluate the effect of lactoferrin on biofilm formation, P. aeruginosa expressing green fluorescent protein (GFP) was grown in continuous culture flow cells and biofilm development followed over time. Flow cell chambers were continuously perfused with biofilm medium with or without Ga(NO₃)₃.

Figure 9:
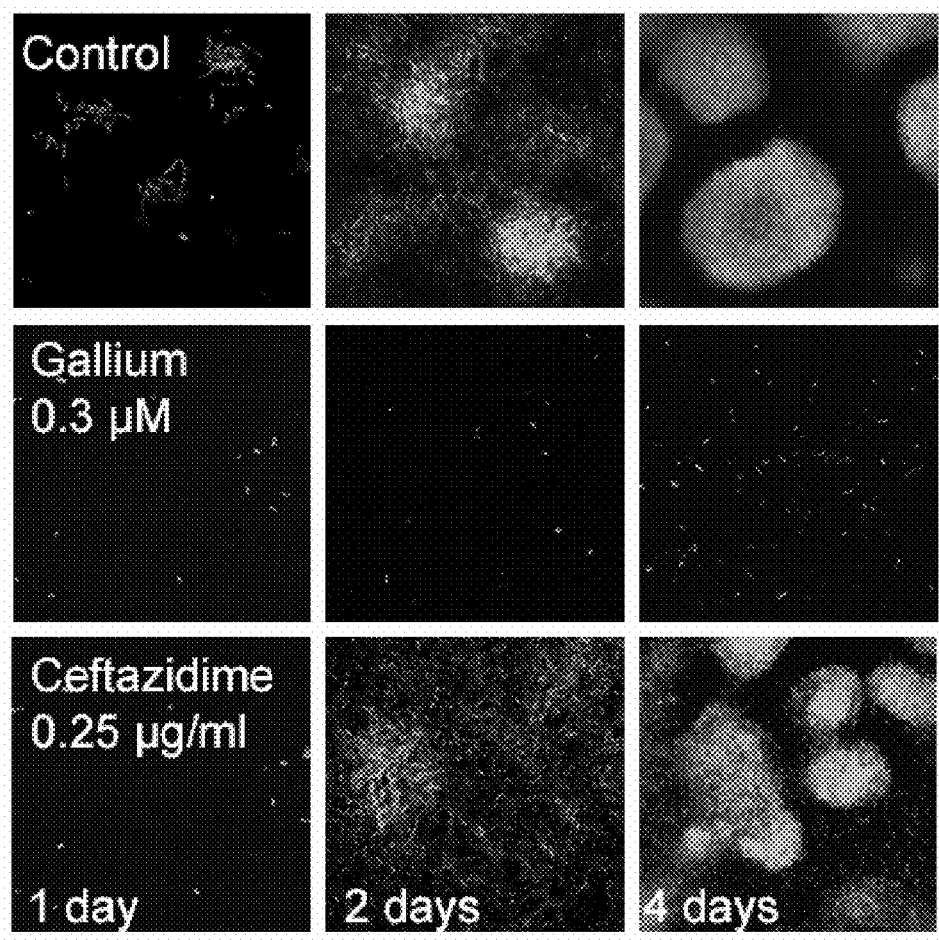
FIG. 9. Confocal microscopic images of GFP-labeled P. aeruginosa in biofilm flow cells perfused with control (top) medium and medium containing 0.3 μM Ga(NO$_3$)$_3$ (middle), and 0.25 μg/ml ceftazadime (bottom). Images were obtained 1, 2, and 4 days after inoculating the flow cells. Images are top-down views (x-y plane).

In medium without gallium (FIG. 9), typical stages of biofilm development were observed. Initially, bacteria attached to the surface. After 2 days of growth, microcolonies (clusters of cells that form early in biofilm development) were evident. By day 4, pillar shaped biofilms had formed. Gallium disrupted this pattern of development. In the presence of Ga(NO₃)₃, bacteria attached, but the subsequent steps in biofilm formation were inhibited (FIG. 9). Even after a prolonged incubation, the bacteria did not assemble into differentiated biofilm structures; in the presence of gallium they remained in a thin layer.

Because of the dramatic effect of gallium on biofilm formation, additional experiments to examine whether sub-inhibitory concentrations of other antimicrobial agents behaved similarly were performed. FIG. 9 shows that sub-inhibitory concentrations of the anti-pseudomonal antibiotic ceftazidime did not inhibit biofilm development. This suggests that biofilm inhibition is not a general effect of antibiotics at sub-inhibitory concentrations. The mechanism by which gallium exerts this effect will be studied.

Example 9

Gallium Kills Established Biofilms

Figure 10A:
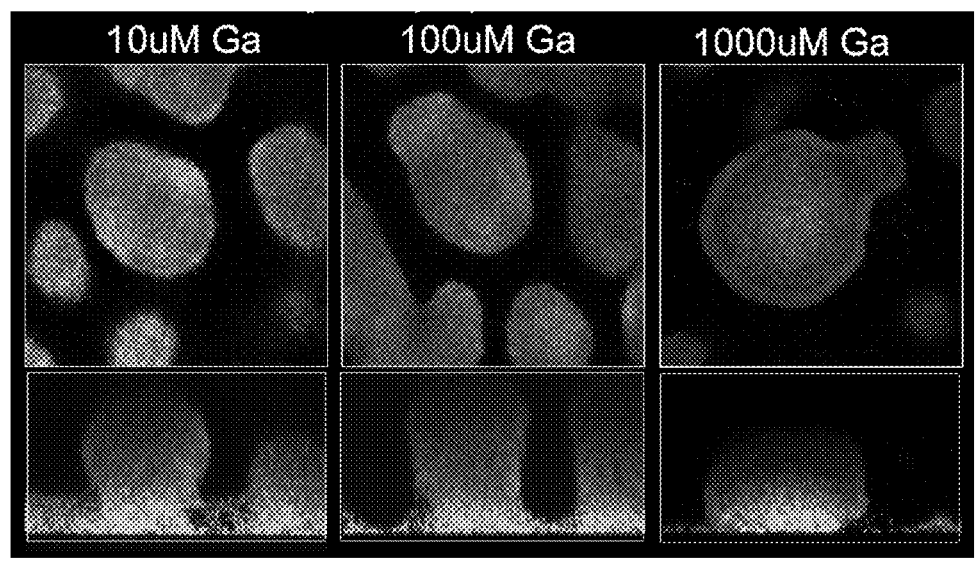
FIGS. 10A-10D. Gallium kills established biofilms. Three-day-old biofilms were exposed to gallium in concentrations of 10 μM, 100 μM, and 1000 μM. Biofilm viability was assessed with propidium iodide, and observations were recorded at 12 hours (FIG. 10A), 24 hours (FIG. 10B), 48 hours (FIG. 10C), and 72 hours (FIG. 10D).
Figure 10B:
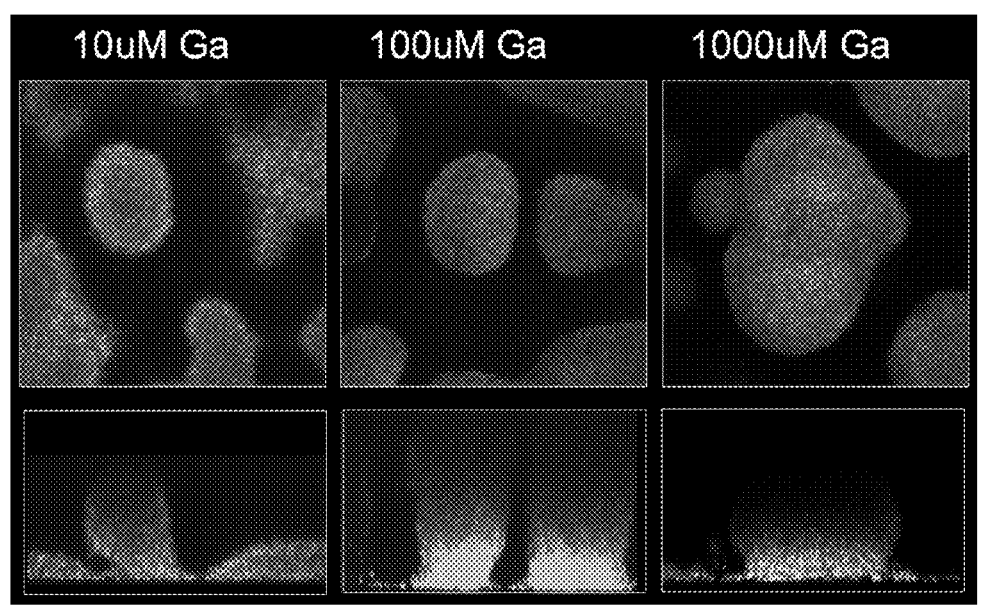
Figure 10C:
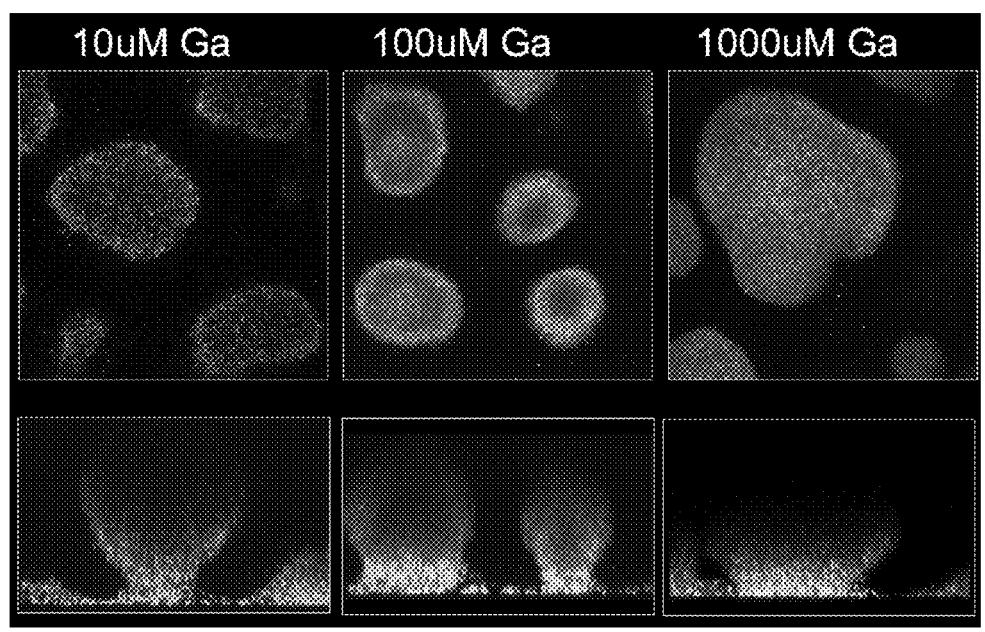
Figure 10D:
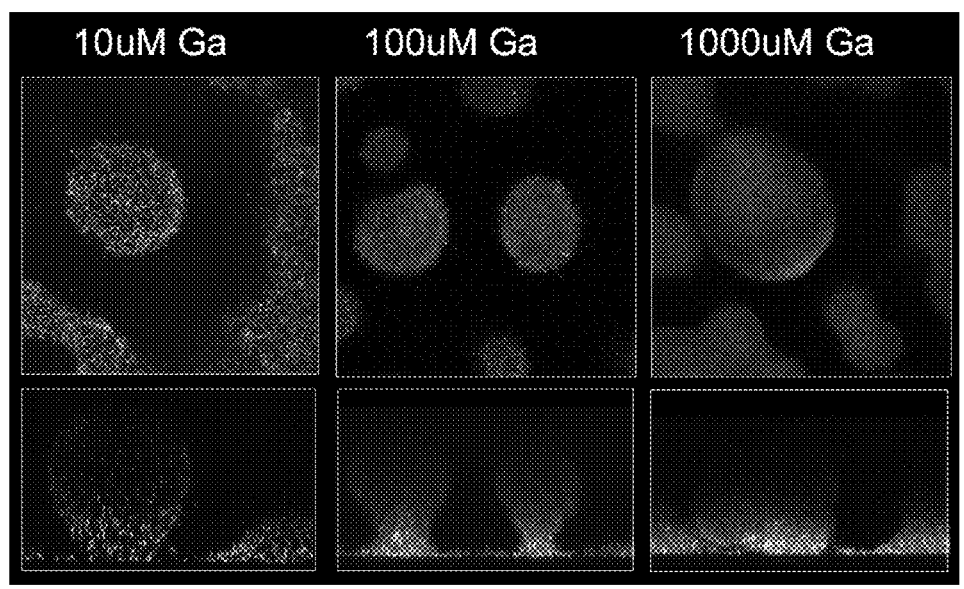

The above data suggesting that gallium inhibits biofilm formation prompted the examination of the potential impact of gallium on established biofilms. Three-day-old biofilms were exposed to gallium in concentrations of 10 μM, 100 μM, and 1000 μM. The biofilm viability was assessed with propidium iodide, and observations were recorded at 12 hours (FIG. 10A), 24 hours (FIG. 10B), 48 hours (FIG. 10C), and 72 hours (FIG. 10D). FIGS. 10A-10D show that gallium kills established biofilms in a time and concentration dependent manner, and it does so at concentrations within peak levels achieved clinically (140-700 μM).

* * *

All of the compositions and/or methods and/or apparatus disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and/or apparatus and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,997,912
U.S. Pat. No. 6,203,822
U.S. Pat. No. 6,267,979
U.S. Pat. No. 6,086,921
U.S. Pat. No. 5,688,516
Adair et al., *Intensive Care Med.*, 25:1072-1076, 1999.
Adair et al., *J. Antimicrob. Chemother.*, 31:689-697, 1993.
Anwar et al., *Antimicrob Agents Chemother.*, 36:1208-14, 1992.
Bauer et al., *Monaldi Arch. Chest Dis.*, 57: 84-87, 2002.
Bergmans et al., *Infect. Control Hosp. Epidemiol.*, 19: 853-855, 1998.
Bernstein, *Pharmacol. Rev.*, 50:665-682, 1998.
Bitton, in *Wastewater Microbiology*, Wiley-Liss, New York, N.Y., 1994.
Chastre et al., *Am. J. Respir. Crit. Care Med.*, 165: 867-903, 2002.

Chitambar, *Semin Oncol.*, 30(2 Suppl 5):1-4, 2003.
Chitambar et al., *Blood*, 72:1930-1936, 1988.
Chitambar et al., *Cancer Res.*, 47:3929-3934, 1987.
Clemens et al., *J. Exp. Med.*, 184:1349-1355, 1996
Costerton et al., *Science*, 284:1318-1322, 1999.
Darouiche et al., *N Engl J. Med.*, 340:1-8, 1999.
Davis et al., *Science*, 280:295-298, 1998.
Drenkard et al., *Nature*, 416:740-743.
Dussurget et al., *Mol. Microbiol.*, 22:535-544, 1996.
Elkins et al., *Appl. Environ. Microbiol.*, 65:4594-4600, 1999.
Evans et al., *J Antimicrob Chemother.*, 27:177-84, 1991.
Fick, *Chest*, 95:206S-213S, 1989.
Fick et al., *Chest*, 96:158-164, 1989.
Flowers et al., *JAMA*, 261:878-83, 1989.
Foster et al., *Cancer Treat Rep.*, 70:1311-1319, 1986.
Freeman et al., *J Antimicrob Chemother.*, 15:258, 1985.
Gale et al., *Cancer Res.*, 24:1012-1020, 1964.
Gorman et al., *Biomaterials*, 22:2741-2747, 2001.
Hubbard et al., *Arch. Microbiol.*, 146:80-86, 1986.
Inglis et al., *J. Clin. Microbiol.*, 27:2014-2018, 1989.
Jonkoff et al., *Br. J. Cancer*, 67:693-700, 1993.
Kamal et al., *JAMA*, 265:2364-8, 1991.
Klempner et al., Hospital infections and health-care epidemiology, In: INFECTIOUS DISEASES: MEDICAL KNOWLEDGE SELF-ASSESSMENT PROGRAM, 2$^{ND}$ EDITION, American College of Physicians, Philadelphia, Pa., pp. 210, 1998.
Koerner, *J. Hosp. Infect.*, 35:83-89, 1998.
Leu et al., *Am. J. Epidemiol.*, 129:1258-1267, 1989.
Levine et al., *Clin. Chest Med.*, 12: 523-543, 1991.
Leyland-Jones, *Semin Oncol.*, 18:16, 1991.
Lode et al., *Intensive Care Med.*, 18 Suppl 1: S24-S27, 1992.
Lyczak et al., *Microbe. Infect.*, 2:1051-1060, 2000.
Mah et al., *Trends Microbiol.*, 9:34-39, 2001.
Maki, In: Bisno A L, Waldovogel F A, editors. Infections associated with indwelling medical devices. 2nd ed. Washington: American Society for Microbiology; p. 155-212, 1994.
Marshall et al., *Semin. Respir. Infect.*, 6:11-18, 1991.
Meynard et al. *J. Infect.* 3(3):176-81, 1999.
Narasimhan et al., *Biochem. Pharmacol.*, 44:2403-2408, 1992.
Olakanmi et al., *Infect. Immun.*, 68:5619-5627, 2000.
Olakanmi et al., *J. Immunol.* 153:2691-2703, 1994.
Platt et al., *J. Hosp. Infect.*, 11:396-397, 1988.
Pollack, In: *Principles and Practice of Infectious Diseases*, Mandell et al. (Eds.), Churchill Livingstone, N.Y., 2310-2335, 2000.
Raad, *Lancet*, 351:893-898, 1998.
Schmitt et al., *Infect. Immun.*, 63:4284-4289, 1995.
Schuster et al., *AIDS*, 8:1437-1441, 1994.
Seligman et al., *Am. J. Hematol.*, 41:232-240, 1992.
Shepp et al., *J Acquir. Immune Defic. Syndr.*, 7:823-831, 1994
Singh et al., *Nature*, 417:552-555, 2002.
Sottile et al., *Crit. Care Med.*, 14:265-270, 1986.
Steelhammer et al,. *Indust. Water Treatm.*, 49-55, 1995.
Stewart et al., *Appl. Environ. Microbiol.*, 66:836-838, 2000
Stickler et al., *Appl Environ Microbiol.*, 64(9):3486-90, 1998.
Suci et al., *Antimicrob Agents Chemother.*, 38:2125-33, 1994.
Todd et al., *Drugs*, 42:261-273, 1991.
Wenzel et al., *N Engl J Med.*, 340:48-9, 1999.
WO 98/09622
WO 03/088914 A2
Yang et al., *J. Bacteriol.*, 179:6408-6415, 1997.
Yang et al., *J. Bacteriol.*, 6738-6743, 1994.

What is claimed:

1. A method of killing an established biofilm in or on a subject comprising:
   (1) identifying a subject that has an established biofilm in or on the subject or has symptoms consistent with having an established biofilm in or on the subject; and
   (2) providing to the subject a gallium-containing composition at a concentration sufficient to kill the established biofilm,
wherein the gallium-containing composition comprises gallium maltolate.

2. The method of claim 1, wherein the biofilm growth formation is bacterial biofilm growth formation.

3. The method of claim 2, wherein the bacterial biofilm growth formation is caused by a *Pseudomonas* species.

4. The method of claim 3, wherein the *Pseudomonas* species is *P. aeruoginosa*.

5. The method of claim 1, wherein the biofilm growth formation is fungi, yeast, or protozoa biofilm growth formation.

6. The method of claim 1, wherein the gallium-containing composition is provided to a subject with a lung infection.

7. The method of claim 6, wherein the lung infection results from cystic fibrosis.

8. The method of claim 1, wherein the gallium-containing composition is provided to a subject with burn wounds.

9. The method of claim 1, wherein the gallium-containing composition is delivered systemically.

10. The method of claim 1, wherein the gallium-containing composition is delivered by aerosol.

11. The method of claim 1, wherein the gallium-containing composition comprises gallium nitrate.

12. The method of claim 1, wherein the gallium-containing composition is delivered topically.

13. A method of killing an established biofilm in or on a subject comprising:
   (1) identifying a subject that has an established biofilm in or on the subject or has symptoms consistent with having an established biofilm in or on the subject; and
   (2) providing to the subject a gallium-containing composition at a concentration sufficient to kill the established biofilm,
wherein the gallium-containing composition is delivered topically; and
wherein the gallium-containing composition is provided to a subject with burn wounds.

* * * * *

UNITED STATES PATENT AND TRADEMARK OFFICE
CERTIFICATE OF CORRECTION

PATENT NO.        : 9,539,367 B2
APPLICATION NO.   : 11/004049
DATED             : January 10, 2017
INVENTOR(S)       : Britigan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 3330 days.

Signed and Sealed this
Twenty-fifth Day of September, 2018

Andrei Iancu
*Director of the United States Patent and Trademark Office*